(12) United States Patent
Endo et al.

(10) Patent No.: US 7,592,371 B2
(45) Date of Patent: Sep. 22, 2009

(54) EXTERNAL PREPARATION

(75) Inventors: Mitsuru Endo, Itano-gun (JP); Keiko Yamasaki, Higashikagawa (JP); Hidetoshi Hamamoto, Itano-gun (JP); Sueko Matsumura, Higashikagawa (JP); Masaki Ishibashi, Naruto (JP)

(73) Assignee: Medrx Co., Ltd., Kagawa (JP)

( * ) Notice: Subject to any disclaimer, the term of this patent is extended or adjusted under 35 U.S.C. 154(b) by 0 days.

(21) Appl. No.: 11/660,393

(22) PCT Filed: Aug. 1, 2005

(86) PCT No.: PCT/JP2005/014468

§ 371 (c)(1),
(2), (4) Date: Feb. 16, 2007

(87) PCT Pub. No.: WO2006/018997

PCT Pub. Date: Feb. 23, 2006

(65) Prior Publication Data

US 2008/0108700 A1 May 8, 2008

(30) Foreign Application Priority Data

Aug. 18, 2004 (JP) ............................. 2004-238167
Jan. 28, 2005 (JP) ............................. 2005-021549

(51) Int. Cl.
*A61K 31/164* (2006.01)
*A61K 31/195* (2006.01)

(52) U.S. Cl. ....................... 514/561; 514/626

(58) Field of Classification Search ....................... None
See application file for complete search history.

(56) References Cited

U.S. PATENT DOCUMENTS

| | | | | |
|---|---|---|---|---|
| 4,748,022 A | * | 5/1988 | Busciglio | ................... 424/539 |
| 4,866,050 A | * | 9/1989 | Ben-Amoz | ................... 514/179 |
| 6,239,177 B1 | | 5/2001 | Mori et al. | |
| 6,429,228 B1 | | 8/2002 | Inagi et al. | |
| 6,432,986 B2 | | 8/2002 | Levin | |
| 2001/0004644 A1 | | 6/2001 | Levin | |
| 2001/0055607 A1 | | 12/2001 | Levin | |
| 2002/0010194 A1 | | 1/2002 | Levin | |
| 2003/0133877 A1 | | 7/2003 | Levin | |
| 2004/0029843 A1 | * | 2/2004 | Lawter | ....................... 514/152 |

FOREIGN PATENT DOCUMENTS

| | | |
|---|---|---|
| EP | 1 405 646 | 4/2004 |
| JP | 6-128153 | 5/1994 |
| JP | 8-295624 | 11/1996 |
| JP | 11-322620 | 11/1999 |
| JP | 2001-503035 | 3/2001 |
| JP | 2001-513483 | 9/2001 |
| JP | 2002-128699 | 5/2002 |
| JP | 2003-252793 | 9/2003 |
| JP | 2004-161625 | 6/2004 |
| WO | 97/28793 | 8/1997 |

* cited by examiner

*Primary Examiner*—Brian-Yong S Kwon
*Assistant Examiner*—Bong-Sook Baek
(74) *Attorney, Agent, or Firm*—Wenderoth, Lind & Ponack, L.L.P.

(57) ABSTRACT

It is an object of the present invention to provide an external preparation having enhanced transdermal penetration of a mast cell degranulation inhibitor. It is also an object of the present invention to provide a method for improving the photostability of a preparation containing a mast cell degranulation inhibitor. The present invention provides an external preparation containing a mast cell degranulation inhibitor and a topical anesthetic. Further, the method for enhancing the photostability of a preparation containing a mast cell degranulation inhibitor according to the present invention includes adding a topical anesthetic thereto.

2 Claims, 1 Drawing Sheet

EXTERNAL PREPARATION

TECHNICAL FIELD

The present invention relates to a method for improving the photostability of an external preparation containing a mast cell degranulation inhibitor and a topical anesthetic as well as a preparation containing a mast cell degranulation inhibitor.

BACKGROUND ART

A human body has a function of removing external substances which have invaded or contacted the body. This function is called the immune system, which is extremely important as a defense system of the human body. The immune system is regulated by the immune regulation system so that it does not respond to the human body's own tissues.

However, if the mechanism of the immune regulation system is destroyed, an excessive response disadvantageous to the human body's own self may occur. The response has adverse effects on the human body such as allergy and sensitivity.

A foreign substance which causes allergy is called an allergen, and various substances such as ticks, pollen, dust, food, and drugs can become an allergen. The expression of allergy differs in each individual, and depending on the affected area, various symptoms occur, such as hives or atopic dermatitis in the case of skin, allergic rhinitis in the case of nose, and bronchitis in the case of bronchus.

In general, allergic symptoms are said to occur in response to the stimulation of an allergen which causes mast cell degranulation, so that a chemical mediator (chemical messenger) is released to trigger an inflammatory response leading to the onset of the symptom. First, a release of histamine, leukotriene, and the like triggers an immediate response such as vasodilation, vascular hyperpermeability, mucus secretion, nerve stimulation, and respiratory stenosis, and then follows a release of cytokine and the like a few hours later, which lets an inflammatory cell roll on and adhere to a vascular wall, migrate to the tissue and be activated, resulting in a delayed response. That is, allergy symptoms are triggered by mast cell degranulation.

The drugs which alleviate and treat such allergy symptoms are antiallergic agents. Antiallergic agents work to suppress inflammatory responses by controlling a release or an action of a chemical mediator such as histamine.

Examples of the well known antiallergic agents may include histamine antagonists, mast cell degranulation inhibitors, chemical synthesis inhibitors, and antibody production inhibitors. In these antiallergic agents, mast cell degranulation inhibitors are drugs capable of suppressing, as described above, allergic episodes at the stage of degranulation.

Conventionally, external steroid preparations have usually been used for allergic skin diseases such as atopic dermatitis, and great therapeutic effects have been achieved. However, the use of steroid requires a greatest care, and depending on the conditions, for example, the type of steroid, dosage, the number of doses, and whether it is chronically administered or not, and the like, side effects may occur, such as skin atrophy, dry skin, infection induction resulting from a decrease in immunity, photosensitivity, and dyschromia. In addition, a special care must be taken when steroid is given to infants or elderly persons who have delicate skin.

Therefore, mast cell degranulation inhibitors such as tranilast and sodium cromoglycate are expected to be drugs which replace the above-described steroid, and have been used for skin diseases such as atopic dermatitis. In such allergic skin diseases, since degranulation from mast cells occurs in a diseased area of the skin, a topical administration directly to the diseased area of the skin may be preferred.

Further, drugs such as tranilast have been observed to cause serious side effects such as hepatic dysfunction and renal dysfunction by oral administration (Pharmaceutical Products Interview Form (Revised in April, 2004); Sekiseed Capsules, Sekiseed Dry Syrup). Therefore, in order also to alleviate such side effects, the development of external preparations has increasingly been desired.

However, mast cell degranulation inhibitors are at present commercially available only in such forms as a preparation for oral or transmucosal administration or as an ophthalmic solution (e.g., Pharmaceutical Products Interview Form (Revised in April, 2004); Sekiseed Capsules, Sekiseed Dry Syrup). It is because many of the mast cell degranulation inhibitors have low transdermal penetration.

Also, in the mast cell degranulation inhibitors, there are drugs having extremely poor photostability. Accordingly, they are not suitable for external preparations which are directly affected by light. For example, tranilast exemplified as above is considerably unstable to light (Pharmaceutical Products Interview Form (Revised in April, 2004); Sekiseed Capsules, Sekiseed Dry Syrup). Therefore, even if tranilast is administered as an external preparation on the diseased area of skin, a considerable decrease in the amount of tranilast contained therein by light exposure may occur, and the decomposed matter of tranilast and the like may be absorbed in the body, so that there is a risk of causing unexpected adverse effects within a living body such as allergic reaction.

In order to ensure the stability of tranilast to light exposure, for example, methods in which tranilast is used as the dosage form of capsule or in which tranilast is stored with protection from light have been studied (Pharmaceutical Products Interview Form (Revised in April, 2004); Sekiseed Capsules, Sekiseed Dry Syrup). However, in these methods, although the stability of the preparation itself when stored is considered, there is no disclosure about the stability of the preparation after administration. In the case where tranilast takes a dosage form in which it is not exposed to light after administration, for example, such as an internal drug or an ophthalmic solution, it is sufficient to ensure the stability of the preparation as described above. However, in the case where tranilast is administered on the diseased area of skin as an external preparation such as an ointment, although it may be an idea to cover the diseased area to protect from light after the external preparation is applied, such protection from light may become extremely difficult depending on the diseased area of skin.

Accordingly, with respect to tranilast, it is difficult to formulate this drug as an external preparation because of its low transdermal penetration, and even if an external preparation of tranilast is successfully formulated, an improvement of photostability will be required.

Incidentally, in Japanese Patent Laid-open Publication No. 2001-513483 (CLAIMS, [0038]), the use of a long-acting topical anesthetic in order to suppress cerebral neurovascular disorders is described, and specific examples of the topical anesthetic may include bupivacaine. Also, in Japanese Patent Laid-open Publication No. 2001-513483, there is a description that a mast cell degranulation inhibitor may be added to the above-described pharmaceutical composition. However, the technique according to Japanese Patent Laid-open Publication No. 2001-513483 has an object of alleviating the headache, and it is a technique in which the medical composition is administered transnasally, and it is not intended for skin diseases or transdermal administration. Furthermore, a mast cell degranulation inhibitor is only an example of substances which is supplementarily added in order to suppress histamine headache in various types of headaches, and there is no description of a specific preparation containing both a mast cell degranulation inhibitor and a topical anesthetic.

Also, there is a disclosure of a technique in which propolis and a balsaminaceous plant, both of which are said to have mast cell degranulation inhibition action, are used in combination as an external preparation (Japanese Patent Laid-open Publication No. 11-322620). In these ingredients, propolis is considered to also have topical anesthetic action. However, they only enhance antiallergic action by combining mast cell degranulation inhibition action of the two.

Incidentally, an NSAID (i.e., nonsteroidal anti-inflammatory drug) is used as an external preparation for skin diseases as a substitute for steroid. Techniques of producing a preparation of the NSAID by combining an NASID with a topical anesthetic are disclosed, for example, in following literatures: Japanese Patent Laid-open Publication No. 2003-252793 discloses a technique of enhancing anti-inflammatory and analgesic effects and Japanese Patent Laid-open Publication No. 2002-128699 discloses a technique of increasing transdermal penetration, while EP 1 405 646 A2 discloses a technique of preparing a salt of an NSAID and a topical anesthetic.

However, the above literatures are related to the technique of combining an NSAID with a topical anesthetic, and neither tranilast nor degranulation inhibitors are disclosed.

DISCLOSURE OF THE INVENTION

As described above, since mast cell degranulation inhibitors have low transdermal penetration, there is no example that it is developed as an external preparation. However, by formulating a mast cell degranulation inhibitor as an external preparation, direct administration in skin diseases becomes possible, and serious side effects on body organs in oral administration can be prevented. Also, some mast cell degranulation inhibitors are extremely poor in photostability, which is one of the reasons that these drugs are not developed as an external preparation.

The present invention has been achieved in view of the above circumstances. An object of the present invention is to provide an external preparation having enhanced transdermal penetration of a mast cell degranulation inhibitor. It is also an object of the present invention to provide a method for improving the photostability of a preparation containing a mast cell degranulation inhibitor.

The present inventors have intensively studied for attaining the above objects, and have accomplished the present invention with a discovery that the combined use of a topical anesthetic can considerably improve transdermal penetration of a mast cell degranulation inhibitor.

That is, the external preparation of the present invention that has attained the above objects comprises a mast cell degranulation inhibitor and a topical anesthetic.

According to a preferred embodiment of the present invention, the mass ratio of the mast cell degranulation inhibitor with respect to the topical anesthetic is from 0.1 to 15. By properly adjusting the addition ratio of the mast cell degranulation inhibitor to the topical anesthetic, the transdermal penetration of the mast cell degranulation inhibitor can further be improved.

It is a preferred embodiment of the present invention that the mast cell degranulation inhibitor is tranilast. Formulating tranilast as an external preparation has specifically been desired because there may probably be a risk of side effects on body organs if this drug is taken orally. However, the instability of tranilast to light and its possibility of affecting adversely within a living body have made the external use thereof even more difficult. However, by adding a topical anesthetic, tranilast can considerably improve its transdermal penetration as well as its stability to light exposure. As a result, tranilast having a risk of side effects can be used externally, which is highly beneficial.

Also, it is another preferred embodiment of the present invention that the topical anesthetic is lidocaine, and the external preparation of the present invention may preferably further comprise a base for ointment. Formulating it as an ointment, it can appropriately be applied to the diseased area without dripping regardless of the size of the diseased area of skin.

The method for improving the photostability of a preparation containing a mast cell degranulation inhibitor according to the present invention comprises adding a topical anesthetic thereto.

BEST MODE FOR CARRYING OUT THE INVENTION

Figure 1:
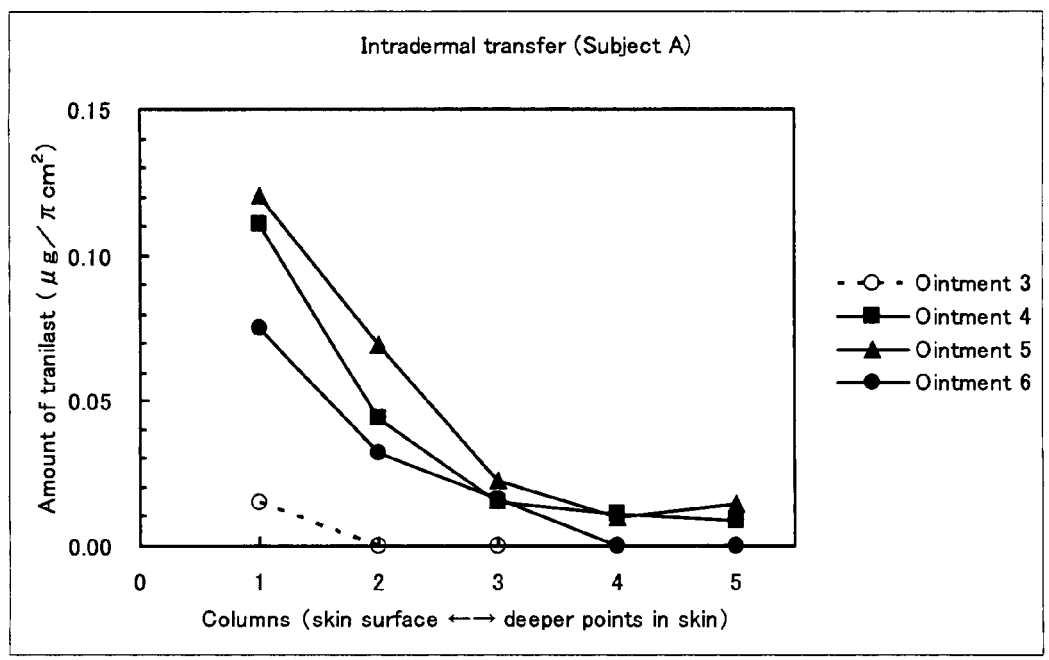
FIG. 1 is a graph showing the intradermal transfer of tranilast in Example 2 (Subject A).

The external preparation of the present invention comprises a mast cell degranulation inhibitor and a topical anesthetic. By containing a mast cell degranulation inhibitor and a topical anesthetic, the transdermal penetration of the mast cell degranulation inhibitor can be improved.

The mast cell degranulation inhibitor to be used in the present invention is not particularly limited, so long as it is used as a medical product. Examples thereof may include sodium cromoglycate, tranilast, amlexanox, repirinast, tazanolast, pemirolast potassium, ketotifen fumarate, azelastine hydrochloride, oxatomide, and ibudilast. One kind, or two or more kinds, selected from these drugs may preferably be used.

In these drugs, tranilast may particularly be preferred. Tranilast has a considerable risk of side effects on body organs if taken orally, so that the use of this drug as an external preparation has particularly been desired. However, tranilast is a drug which is unstable to light (Pharmaceutical Products Interview Form (Revised in April, 2004); Sekiseed Capsules, Sekiseed Dry Syrup), and the risk of affecting adversely within a living body has made its use as an external preparation even more difficult.

However, by containing tranilast and a topical anesthetic, the transdermal penetration of tranilast can be improved, making it possible to formulate this drug as an external preparation, while at the same time a decrease in the amount of tranilast contained by light exposure can be alleviated. Accordingly, possible side effects caused by taking this drug orally can be avoided, which is highly beneficial.

Tranilast is a compound with the chemical name "N-(3,4-Dimethoxycinnamoyl) anthranilic acid", used for treating bronchial asthma, allergic rhinitis, atopic dermatitis, and the like by the action of suppressing the generation of a chemical mediator which triggers allergic reaction (i.e., mast cell degranulation inhibition action), and expressed by the following chemical formula:

[Chemical Formula 1]

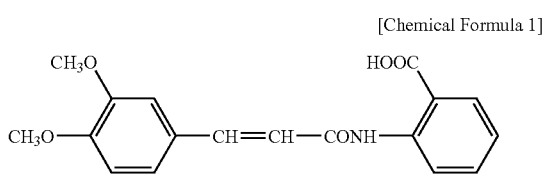

Tranilast can be used per se or as an alkali metal salt which is pharmacologically acceptable such as a sodium salt and a potassium salt.

The topical anesthetic to be used in the present invention is not particularly limited, so long as it is usually used for medical purposes. Examples of the topical anesthetic may include lidocaine, tetracaine, procaine, dibucaine, benzocaine, bupivacaine, mepivacaine, and pharmacologically acceptable salts thereof. At least one or more of these topical anesthetics can be used, but in these topical anesthetics, lidocaine and salts thereof may be preferred. Also, any of the compound and salts thereof used as the topical anesthetic may be employed, regardless of whether the mast cell degranulation inhibitor is in free form or in salt form, and if, for example, the free form of the mast cell degranulation inhibitor is used, the free form of the above compound may preferably be used as a topical anesthetic.

The mass ratio of the topical anesthetic to the mast cell degranulation inhibitor is not particularly limited, but for example, may preferably be 0.1 or higher, more preferably 0.35 or higher, still more preferably 0.7 or higher, and may preferably be 15 or lower, more preferably 12 or lower, still more preferably 10 or lower. When the mass ratio of the topical anesthetic is lower than 0.1, transdermal penetration may be unable to be improved. In contrast, when it is higher than 15, the improvement effect of transdermal penetration may reach the plateau, and therefore, a further improvement may be unable to be obtained, which is undesirable in view of cost. As described above, when the mass ratio of the topical anesthetic ranges from 0.1 to 15, the stability of tranilast to light exposure can sufficiently be improved.

To the external preparation of the present invention, depending on its dosage form, any of the additives well known to those skilled in the art which is usually used can be added. Examples of such an additive may include bases, fatty acids or derivatives thereof, alcohols, surfactants, suspending agents, thickeners, solvents, solubilizing agents, inorganic particles, diluents, lubricants, stabilizing agents, moisturizers, buffer agents, pH adjusters, colorants, flavors, bonding agents, disintegrants, and propellants.

Examples of the bases may include oil bases or hydrophobic base components, hydrophilic bases or hydrophilic base components, or gel bases. Examples of the oil base or hydrophobic base component may include rubbers such as natural rubber, isoprene rubber, polyisobutylene, styrene-isoprene-styrene block copolymer, styrene-butadiene-styrene block copolymer, styrene-ethylene-butylene-styrene block copolymer, (meta)alkyl acrylic acid ester (co)polymer, polyacrylic acid ester, methacrylic acid ester, polyisobutylene, polybutene, and liquid polyisoprene; and oils such as petrolatum, cetyl alcohol, bees wax, white beeswax, lanolin, purified lanolin, liquid paraffin, paraffin wax, plastibase containing liquid paraffin and polyethylene, silicone oil, triglyceride, squalene, microcrystalline wax, and spermaceti.

Examples of the hydrophilic bases or aqueous base components may include hydrophilic fatty acid esters such as glycerin esters of saturated fatty acids and water-soluble polymers such as polyethylene glycol. Examples of the gel base component may include carboxy vinyl polymers, starch acrylate, sodium polyacrylate, tragacanth, alginic acid salts, cellulose derivatives such as methylcellulose, carmellose, carmellose sodium, hydroxypropyl cellulose, and hydroxypropyl methylcellulose; colloidal clays made of silicates, such as bentonite and veegum; and water soluble basic substances such as carboxy vinyl polymers, polyvinyl alcohol, polyvinylpyrrolidone, alkali hydroxides, and alkanolamines.

Examples of the fatty acids or derivatives thereof may include higher fatty acids such as oleic acid and stearic acid, or salts thereof; esters of higher fatty acids such as caprylic acid, capric acid, myristic acid, palmitic acid, stearic acid, and oleic acid with monovalent aliphatic alcohols (e.g., isopropyl myristate, isopropyl palmitate, isopropyl stearate, and decyl oleate); triglyceride such as caprylic acid triglyceride, caproic triglyceride, peanut oil, castor oil, cacao seed oil, hydrogenated oils and fats (e.g., hydrogenated castor oil); and fatty acid esters of polyvalent alcohols, such as pentaerythritol fatty acid esters. Examples of the esters of polyvalent carboxylic acids and alcohols may include esters of polyvalent carboxylic acids such as adipic acid and sebacic acid with monovalent aliphatic alcohols (e.g., ethyl adipate and diisopropyl adipate).

Examples of the alcohols may include higher alcohols such as benzyl alcohol, lauryl alcohol, myristyl alcohol, cetyl alcohol, stearyl alcohol, cetostearyl alcohol, and 2-octyldodecanol; lower alcohols such as ethanol and isopropanol; or polyhydric alcohols such as ethylene glycol, glycerine, propylene glycol, and 1,3-butylene alcohol.

Examples of the surfactants may include natural emulsifying agents such as gum arabic, gelatin, tragacanth, lecithin, and cholesterol; anionic surfactants such as soap and sodium alkylsulfate; nonionic surfactants such as polyoxyethylene sorbitan fatty acid esters, e.g., monooleyl polyoxyethylene sorbitan, glycerine fatty acid esters, e.g., polyoxyethylene castor oil derivatives, polyoxyethylene hydrogenated castor oil, glycerine monostearate, and sorbitan monoolate, sorbitan fatty acid esters, e.g., sorbitan monostearate and sorbitan sesquioleate, polyoxyethylene higher alcohol ethers, e.g., polyoxyethylene cetyl ether, polyoxyethylene alkylphenols, and polyoxyethylene oxypropylene copolymers (e.g., Pluronic); cationic surfactants such as cetyltrimethylammonium chloride; and amphoteric surfactants.

Examples of the suspending agents or thickeners may includes polysaccharides such as gum arabic, tragacanth, pullulan, locust bean gum, tamarind gum, pectin, xanthan gum, guar gum, and carrageenan; methyl cellulose, carmellose, carmellose sodium, polyvinyl alcohol, polyvinylpyrrolidone, acrylic acid copolymers, carboxy vinyl polymers, and colloidal microcrystalline cellulose.

Examples of the solvents may include water, propylene glycol, butylene glycol, isopropanol, ethanol, glycerine, diethyl sebacate, isopropyl myristate, diisopropyl adipate, myristyl palmitate, stearyl stearate, myristyl myristate, ceryl lignocerate, lacceryl glycerophosphate, and lacceryl laccerate.

Examples of the solubilizing agents may include carmellose sodium, propylene glycol, polysorbate 80, sodium benzoate, benzyl benzoate, urethane, monoethanolamine, diethanolamine, glycerine, sodium salicylate, diethyl acetamido, sodium hydroxide, sodium carbonate, urea, N-hydroxyethyl lactamide, and monomethyl acetamide.

Examples of the inorganic particles may include talc, silicic anhydride, calcium carbonate, magnesium carbonate, colloidal silica, and bentonite.

Examples of the diluents may include sugar such as white sugar; sugar alcohols such as mannitol; starch derivatives such as dextrin; cellulose derivatives such as crystalline cellulose; and inorganic substances such as calcium phosphate. Examples of the lubricants may include stearic acid metal salts such as calcium stearate and magnesium stearate; laurylsulfates such as magnesium laurylsulfate; and starch derivatives described above as the diluents.

Examples of the stabilizing agents may include preservatives and antioxidants. Examples of the preservatives may include p-hydroxybenzoic acid esters such as methyl paraben and propylparaben; alcohols such as chlorobutanol, benzyl alcohol, and phenylethyl alcohol; thimerosal, acetic anhydride, and sorbic acid. Examples of the antioxidants may include sodium hydrogensulfite, L-ascorbic acid, sodium ascorbate, butylhydroxyanisol, butyl hydroxytoluene, propyl gallate, tocopherol acetate, and dl-α-tocopherol.

Examples of the moisturizers may include polyhydric alcohols such as glycerine, propylene glycol, butylene glycol, and sorbitol.

Also, in addition to these additives, the buffer agents, pH adjusters, colorants, flavors, bonding agents, disintegrants, and the like may be added, if necessary, and further, for example, mentha oil, 1-menthol, camphor, thymol, tocopherol acetate, glycyrrhetinic acid, nonylic acid vanillylamide, and capsicum extract may also be added.

Other than these additives, medical products having other medical effects can further be added, so long as they do not prevent the operation and effect of the external preparation of the present invention.

The additive exemplified above may appropriately be selected depending on the dosage form of the external preparation of the present invention, and the amount of these additives to be added may also appropriately be selected within a range which is usually used, depending on the dosage form of each preparation.

The dosage form of the external preparation of the present invention is not particularly limited, so long as it can be applied topically on the skin. Examples thereof may include ointment, cream, gel, cataplasm, tape, lotion, aerosol, plaster, adhesive preparation, liquid, and liniment. In these dosage forms, ointment, cream, gel, cataplasm, or tape may be preferred, and ointment may particularly be preferred because it can properly be applied to the diseased area without dripping regardless of the size of the diseased area of skin. When ointment is prepared, a base can appropriately be selected for use from the above additives.

Next, a method for preparing the external preparation of the present invention will be explained. The external preparation of the present invention can be prepared using any of the suitable methods well known to those skilled in the art, and the preparation method is not particularly limited. For example, a mast cell degranulation inhibitor and a topical anesthetic may be added to any of the suitable bases well known to those skilled in the art, such as ones described above, and further, other suitable additives described above may be added and mixed to obtain the external preparation of the present invention. It can be heated, if necessary.

The external preparation of the present invention can be applied to a diseased area of skin, for example, by application, inunction, or splay, depending on the dosage form. The amount of the external preparation to be applied to the diseased area can be selected according to the amount of the active ingredient contained; for example, it can be applied once or twice per day and the number of doses is not particularly limited.

The external preparation of the present invention described above has enhanced transdermal penetration. Also, when the photostability of a mast cell degranulation inhibitor which is a main drug is poor, it can be improved and administration thereof as an external preparation becomes possible.

The present invention will be explained below in detail by reference to Examples, but the present invention is not limited to these Examples. The present invention can be put into practice after appropriate modifications or variations within a range meeting the gists described above and later, all of which are included in the technical scope of the present invention.

EXAMPLES

Example 1

Examination (1) of Ointment Containing Mast Cell Degranulation Inhibitor

Production Example 1: Preparation of Ointment 1

Ointment 1 containing tranilast and a topical anesthetic (lidocaine) was prepared by the formulation shown in Table 1. Specifically, tranilast, lidocaine, diethyl sebacate, concentrated glycerin, and propylene glycol were mixed with heating at 80° C., so that they became dissolved; and then, white petrolatum and methyl paraoxybenzoate were added thereto, followed by mixing to obtain ointment 1.

TABLE 1

|  | Ointment 1 | Ointment 2 |
| --- | --- | --- |
| Tranilast methyl | 2 | 2 |
| Lidocaine | 4 | — |
| Propylene glycol | 5 | 5 |
| Diethyl sebacate | 2 | 2 |
| Conc. glycerin | 15 | 15 |
| Paraoxybenzoate | 0.15 | 0.15 |
| White petrolatum | Residue | Residue |
| Total | 100 | 100 |

Unit: % by mass

Production Example 2: Preparation of Ointment 2

An ointment of Production Example 2, containing tranilast but containing no topical anesthetic, was prepared according to the formulation shown in Table 1. Specifically, tranilast, diethyl sebacate, concentrated glycerine, and propylene glycol are mixed with heating at 80° C., so that they became dispersed; and then, white petrolatum and methyl paraoxybenzoate were added, followed by mixing to obtain ointment 2.

Test Example 1: Transdermal Penetration Test

Ointments 1 and 2 were applied on a circular area having a diameter of 2 cm of each arm of three subjects in an amount of 0.5 g, respectively. After 12 hours, the ointment which had been applied was wiped off, and an adhesive tape was put on the surface of the skin of each subject, and then removed. Samples were prepared by repeating 20 times this process of putting on and removing the adhesive tape. Tranilast was extracted from the samples, and using high-performance liquid chromatography, the amount of tranilast was measured, from which the amount of tranilast transferred intradermally was calculated. The results are shown in Table 2.

TABLE 2

|  | Subject 1 | Subject 2 | Subject 3 |
|---|---|---|---|
| Ointment 1 (containing lidocaine) | 5.58 | 1.64 | 7.00 |
| Ointment 2 (containing no lidocaine) | 0.67 | 1.07 | 1.12 |

Unit: μg/πcm$^2$

As shown in Table 2, ointment 1, which is an external preparation of a mast cell degranulation inhibitor containing a topical anesthetic, was considerably high in transdermal penetration compared with ointment 2 containing no topical anesthetic. The transdermal penetration of drugs differs in each individual, and transdermal penetration in subject 2, who had the lowest transdermal penetration, was improved up to approximately 1.5 times higher compared with the case of using an external preparation containing no lidocaine.

Example 2

Examination (2) of Ointment Containing Mast Cell Degranulation Inhibitor

Production Example 3: Preparation of Ointment 3

Ointment 3 containing tranilast but containing no topical anesthetic was prepared according to the formulation shown in Table 3. Specifically, propylene glycol, crotamiton, polyvinylpyrrolidone, and light anhydrous silicic acid were added to tranilast, and these ingredients were mixed with heating at 80° C., so that they became dispersed; and then, gelled hydrocarbon and methyl paraoxybenzoate were added, followed by mixing to obtain ointment 3.

TABLE 3

|  | Ointment 3 | Ointment 4 | Ointment 5 | Ointment 6 |
|---|---|---|---|---|
| Tanilast | 2 | 2 | 2 | 2 |
| Lidocaine | — | 2 | 2 | 2 |
| Popylene glycol | 30 | 30 | 30 | 30 |
| Stearyl alcohol | — | — | — | 15 |
| Crotamiton | 1 | 1 | 1 | — |
| Polyvinylpyrrolidone | 5 | 5 | 3 | — |
| Light anhydrous silicic acid | 1 | 1 | 1 | 1 |
| Polyoxyethylene hydrogenated castor oil 60 | — | — | 4 | 4 |
| Mono-stearic acid glycerine | — | — | 1 | 1 |
| Paraoxybenzoate | 0.16 | 0.16 | 0.16 | 0.16 |
| White petrolatum | — | — | — | 20 |
| Gelled hydrocarbon | Residue | Residue | Residue | — |
| Purified water | — | — | — | Residue |
| Total | 100 | 100 | 100 | 100 |

Unit: % by mass

Production Example 4: Preparation of Ointment 4

Ointment 4 containing tranilast and a topical anesthetic (lidocaine) was prepared according to the formulation shown in Table 3. Specifically, to tranilast and lidocaine, propylene glycol, crotamiton, polyvinylpyrrolidone, and light anhydrous silicic acid were added, and these ingredients was mixed with heating at 80° C., so that they became dissolved; and then gelled hydrocarbon and methyl paraoxybenzoate were added, followed by mixing to obtain ointment 4.

Production Example 5: Preparation of Ointment 5

Ointment 5 containing tranilast and a topical anesthetic (lidocaine) was prepared according to the formulation shown in Table 3. Specifically, to tranilast and lidocaine, propylene glycol, crotamiton, polyvinylpyrrolidone, light anhydrous silicic acid, polyoxyethylene hydrogenated castor oil 60, and mono-stearic acid glycerine were added, and these ingredients was mixed with heating at 80° C., so that they became dissolved; and then, gelled hydrocarbon and methyl paraoxybenzoate were added, followed by mixing to obtain ointment 5.

Production Example 6: Preparation of Ointment 6

Ointment 6 containing tranilast and a topical anesthetic (lidocaine) was prepared according to the formulation shown in Table 3. Specifically, to tranilast and lidocaine, propylene glycol, stearyl alcohol, light anhydrous silicic acid, polyoxyethylene hydrogenated castor oil 60, and mono-stearic acid glycerine were added, and these ingredients was mixed with heating at 80° C., so that they became dissolved; and then, white petrolatum, purified water, and methyl paraoxybenzoate were added, followed by mixing to obtain ointment 6.

Test Example 2: Transdermal Penetration Test

Ointment 3, 4, 5, and 6 were applied on a circular area having a diameter of 1.5 cm of each arm of two subjects of A and B in an amount of 0.02 g, respectively. After 12 hours, the ointment applied on the surface of the skin was wiped off, and a tape was put on the surface of the skin so that the part except for the circular area where the ointment had been put was covered. Next, the sampling of samples was carried out by putting and removing the adhesive tape only on and from the above circular area. Since there was a possibility that remaining tranilast on the surface of the skin might be mixed in, the first two pieces were discarded. Thereafter, 5 pieces of adhesive sheet were used to carry out sampling 5 times, and the samples obtained in 5 times were put together as one specimen (column 1). This operation was repeated to give 4 columns to obtain samples for columns 1 to 5 for each of subjects A and B. After tranilast was extracted from each sample by using methanol, the amount of tranilast was measured by high-performance liquid chromatography, and the amount of intradermally transferred tranilast was calculated. The results are shown in FIGS. 1 and 2.

Figure 2:
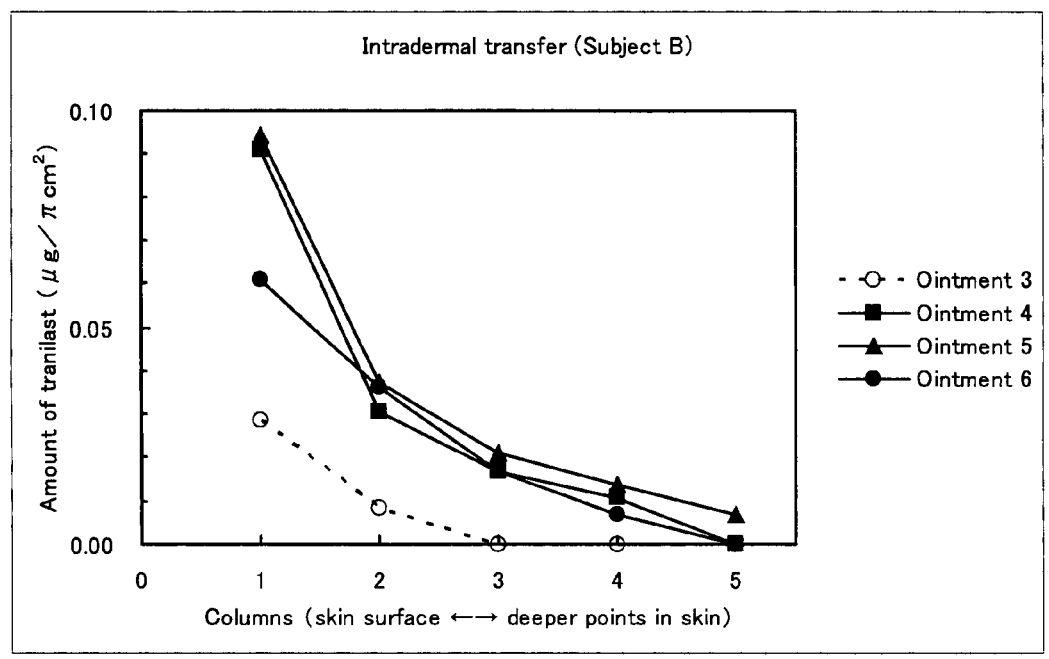
FIG. 2 is a graph showing the intradermal transfer of tranilast in Example 2 (Subject B).

In FIGS. 1 and 2, columns 1 to 5 represent each of the sampling points. Column 1 shows that the sampling was carried out on the surface of the skin, and that, as moving toward column 5, sampling point gradually moved toward deeper part of the skin.

As shown in FIGS. 1 and 2, ointments 4, 5, and 6 which are external preparations containing tranilast as a mast cell degranulation inhibitor and lidocaine as a topical anesthetic, proved to have considerably high transdermal penetration compared with ointment 3 containing no topical anesthetic.

Test Example 3: Application Test

In a subject having almost the same symptoms of atopic dermatitis on the right and left arms, ointment 4 containing tranilast and lidocaine as a topical anesthetic was applied on a diseased area of the right arm, and an ointment obtained by removing tranilast from ointment 4 was applied on a diseased area of the left arm, each in a circular area with a radius of 2 cm, to examine their effects. The number and period of application were once per day, after taking a bath for one month, and a questionnaire was carried out every week. Endpoints were "itching, keloid, and inflammation", and the evaluation criteria were as follows: "−1: deteriorated; 0: some effects were observed; 2: considerable effects were observed; and 3: equivalent to normal skin." The results are shown in Table 4.

TABLE 4

|  |  | Itching | Keloid | Inflammation |
|---|---|---|---|---|
| Right arm | After 1 week | 3 | 1 | 2 |
|  | After 2 weeks | 3 | 1 | 3 |
|  | After 3 weeks | 3 | 2 | 3 |
|  | After 4 weeks | 3 | 3 | 3 |
| Left arm | After 1 week | 0 | 0 | 0 |
|  | After 2 weeks | 0 | 0 | 0 |
|  | After 3 weeks | 0 | 0 | 0 |
|  | After 4 weeks | 0 | 0 | 0 |

As shown in Table 4, symptoms of atopic dermatitis (itching, keloid, and inflammation) were found to have improved in one week by applying tranilast ointment 4 containing lidocaine. Specifically, the effect on itching was observed at an early stage. On the other hand, regarding the ointment obtained by removing tranilast, no improvement of the symptoms was observed.

Also, after the above test was completed, the point in which an improvement of the symptoms on the left arm was not observed (the point where the ointment containing no tranilast was applied), the ointment 3 (tranilast ointment containing no lidocaine as a topical anesthetic) was further applied in the same manner for 1 month, but no improvement of the symptoms was observed.

As a result, it was found that symptom improvement effects were attained by containing a topical anesthetic and a mast cell degranulation inhibitor.

Example 3

Examination on Photostability of Tranilast

Production Example 7: Preparation of Sample 1

Sample 1 was prepared by adding 0.5% by mass of tranilast, 4% by mass of lidocaine, and 8% by mass of N-methyl-2-pyrrolidone, and mixing these ingredients with heating, followed by adding 87.5% by mass of propylene glycol to become 100% by mass in total and mixing with stirring.

Production Example 8: Preparation of Sample 2

Sample 2 was prepared by adding 8% by mass of N-methyl-2-pyrrolidone to 0.5% by mass of tranilast and mixing these ingredients with heating, followed by adding 91.5% by mass of propylene glycol to become 100% by mass in total and mixing with stirring.

Evaluation of stability to light exposure: The samples were placed under a fluorescent light (about 3,000 Lux), and the amount of tranilast in each sample was measured by high-performance liquid chromatography after two and four days from the exposure to the fluorescent light. Further, samples were placed under direct sunlight, and after 2 and 6 hours from the exposure to direct sunlight, the amount of tranilast in each sample was measured by high-performance liquid chromatography.

Using samples 1 and 2 prepared in Production Examples 7 and 8, the evaluation of stability to light exposure was carried out. The results are shown in Tables 5 and 6.

TABLE 5

|  | Sample 1 | Sample 2 |
|---|---|---|
| After 2 days from exposure to fluorescent light | 98.6% | 94.1% |
| After 4 days from exposure to fluorescent light | 97.6% | 88.6% |

Numerical values: the amounts of tranilast contained with time relative to the amount (100%) of tranilast contained at the start

TABLE 6

|  | Sample 1 | Sample 2 |
|---|---|---|
| After 2 hours from exposure to direct sunlight | 88.5% | 61.6% |
| After 6 hours from exposure to direct sunlight | 86.2% | 57.4% |

Numerical value: the amount of tranilast contained with time relative to the amount (100%) of tranilast contained at the start As shown in Table 5, the amount of tranilast contained in sample 1 was 98.6% after two days from the exposure to the fluorescent light, and 97.6% after four days from the exposure to fluorescent light. The amount of tranilast contained in sample 2 was 94.1% after two days from the exposure to fluorescent light, and 88.6% four days after the exposure to fluorescent light. As a result, compared with sample 2 of the present invention containing no topical anesthetic, a decrease in the amount of tranilast contained by the exposure to fluorescent light in sample 1 containing the topical anesthetic was suppressed considerably.

As shown in table 6, the amount of tranilast contained in sample 1 was 88.5% after two hours from the exposure to sunlight, and 86.2% after six hours from the exposure, and the amount of tranilast contained in sample 2 was 61.6% after two hours from the exposure to direct sunlight, and 57.4% after six hours from the exposure. As a result, compared with sample 2 of the present invention containing no topical anesthetic, a decrease in the amount of tranilast contained by the exposure to direct sunlight in sample 1 containing the topical anesthetic was suppressed considerably.

From these results, it was found that the external preparation of the present invention exhibits considerably improved transdermal penetration by containing a mast cell degranulation inhibitor and a topical anesthetic. Also, it was found that, when the mast cell degranulation inhibitor is tranilast, a decrease in the amount of tranilast contained by light exposure can considerably be suppressed; in other words, the stability to light exposure can significantly be improved.

INDUSTRIAL APPLICABILITY

The external preparation of the present invention can considerably enhance the transdermal penetration of a mast cell degranulation inhibitor by containing a topical anesthetic.

Accordingly, a mast cell degranulation inhibitor can topically be administered directly to a diseased area, and the effects of the drug can sufficiently be exhibited.

Also, the present invention makes it possible to prepare an external preparation of a mast cell degranulation inhibitor which has conventionally been difficult to be formulated as an external preparation because of its low transdermal penetration, and therefore, used only as an orally administered drug or the like; therefore, an appropriate administration, that is, a topical administration to the diseased area suffering from skin diseases, was impossible and the possibility of side effects on internal body organs was unable to be avoided.

Further, according to the present invention, the photostability of a mast cell degranulation inhibitor which is low in photostability can considerably be enhanced.

The invention claimed is:

1. A transdermal preparation comprising tranilast and lidocaine, wherein a mass ratio of lidocaine to tranilast is 0.7 to 10 to improve stability of tranilast to light exposure and the stability of tranilast to light exposure is at least 88.5% in terms of an amount of tranilast contained in the preparation after two hours from light exposure.

2. The transdermal preparation according to claim 1, further comprising a base for ointment.

* * * * *